United States Patent
Maillard

(10) Patent No.: US 9,414,908 B2
(45) Date of Patent: Aug. 16, 2016

(54) LIQUID FORMULATION FOR OPHTALMIC DEVICES

(75) Inventor: Mathieu Maillard, Lyons (FR)

(73) Assignee: PARROT DRONES, Paris (FR)

( * ) Notice: Subject to any disclaimer, the term of this patent is extended or adjusted under 35 U.S.C. 154(b) by 0 days.

(21) Appl. No.: 14/112,244

(22) PCT Filed: Apr. 13, 2012

(86) PCT No.: PCT/EP2012/056846
§ 371 (c)(1),
(2), (4) Date: Nov. 22, 2013

(87) PCT Pub. No.: WO2012/143304
PCT Pub. Date: Oct. 26, 2012

(65) Prior Publication Data
US 2014/0081396 A1     Mar. 20, 2014

Related U.S. Application Data

(60) Provisional application No. 61/476,666, filed on Apr. 18, 2011.

(51) Int. Cl.
| | |
|---|---|
| *A61F 2/16* | (2006.01) |
| *G02B 3/14* | (2006.01) |
| *G02B 26/00* | (2006.01) |
| *G02C 7/08* | (2006.01) |
| *B29D 11/00* | (2006.01) |

(52) U.S. Cl.
CPC ........ *A61F 2/1627* (2013.01); *B29D 11/00009* (2013.01); *G02B 3/14* (2013.01); *G02B 26/005* (2013.01); *G02C 7/085* (2013.01)

(58) Field of Classification Search
CPC ... A61F 2/1613; A61F 2/1616; A61F 2/1624; A61F 2/1635; A61F 2/1648; G02B 26/005; G02B 3/14; G02C 7/085
See application file for complete search history.

(56) References Cited

U.S. PATENT DOCUMENTS

| | | | |
|---|---|---|---|
| 4,731,079 A * | 3/1988 | Stoy | 623/6.58 |
| 4,988,352 A | 1/1991 | Poley | |
| 6,679,605 B2 * | 1/2004 | Zhou et al. | 351/159.01 |
| 8,216,306 B2 * | 7/2012 | Coroneo | 623/6.22 |
| 8,460,376 B2 * | 6/2013 | Donitzky et al. | 623/6.22 |
| 2003/0105522 A1 | 6/2003 | Glazier | |
| 2005/0283164 A1 | 12/2005 | Wu et al. | |
| 2007/0179201 A1 | 8/2007 | Maillard et al. | |
| 2009/0264998 A1 | 10/2009 | Mentak et al. | |

FOREIGN PATENT DOCUMENTS

| | | |
|---|---|---|
| WO | 01/89816 A1 | 11/2001 |
| WO | 2007/107589 A1 | 9/2007 |
| WO | 2007/107686 A1 | 9/2007 |

OTHER PUBLICATIONS

International Search Report for corresponding International Application No. PCT/EP2012/056846, mailed Nov. 21, 2012 (5 pages).

* cited by examiner

*Primary Examiner* — David H. Willse
*Assistant Examiner* — Javier Blanco
(74) *Attorney, Agent, or Firm* — Osha Liang LLP

(57) ABSTRACT

According to a first aspect, the invention relates to an intraocular variable focus implant comprising a non-conducting liquid with a melting temperature above 0° C., a conducting liquid, a liquid interface formed by the non-conducting and conducting liquids, a first electrode in contact with the conducting liquid, a second electrode insulated from the conducting liquid, wherein the liquid interface is movable by electro wetting according to a change in a voltage applied between the first and second electrodes.

8 Claims, 2 Drawing Sheets

LIQUID FORMULATION FOR OPHTALMIC DEVICES

TECHNICAL FIELD OF INVENTION

The present invention relates to an intraocular lens (IOL) having variable optical power and containing two immiscible liquids.

BACKGROUND

During cataract surgery, the patient lens is removed and replaced by a fix plastic lens, which deprives the patient of accommodation capabilities. Intraocular lens (IOL) implants are mostly developed to replace a lens from patients that suffer from cataract. This surgery operation prevents the patient from going blind and many inventions have been developed to provide to the patient the capability of focusing on objects at various distances from the eye.

Usually, the focusing capability for a healthy person is about 15 $m^{-1}$, meaning a focus from infinity to about 6 cm. This range may reduce as the patient ages down to few $m^{-1}$, or diopters.

IOL implants have been developed primarily to replace the patient lens at one fixed focus. Such an implant is folded and inserted in the lens cavity through a tubular means in order to reduce as much as possible the size of the corneal incision. However, such inventions may be limited because patient is only recovering vision at a given focus. Therefore the patient is unable to focus on objects at various distances.

Variable focusing IOL implants have been developed. Many of variable focusing IOL implants are based on the capability of the patient to use the eye's ciliary muscles to vary the focus and, thus, actuate the IOL implant instead of the eye's original lens. Such variable focusing IOL implants may vary the focus by a mechanical displacement of a fixed focus lens, or a lens deformation.

Variable focusing may also be performed using microfluidic means. In such IOL implants, a fluid may be injected from a reservoir into the optical path to deform the interface and, thus, change the optical power of the IOL implant. In such devices, the fluid reservoir may also be connected to the ciliary muscles. Therefore, implying that the ciliary muscles will still have the strength to actuate the device. This is not always the case for patients after a certain age, and especially for patients suffering from presbyopia.

Recently, Varioptic has described an IOL implant based on electrowetting actuation and made of two immiscible liquids on an insulating and hydrophobic surface (see WO2007107589). The IOL implant is encapsulated in a foldable structure, such that the device may be folded during the implantation process. However, the fluids used in the IOL device, and how to fold the device without disturbing the liquids confinement has been previously undisclosed.

One object of the present disclosure is to provide an IOL implant capable of being folded and unfolded during the implantation process thus minimizing the ocular incision without disturbing the performance of the IOL device.

SUMMARY

In a first aspect, the invention provides an intraocular variable focus implant comprising a non-conducting liquid with a melting temperature above 0° C., a conducting liquid, a liquid interface formed by the non-conducting and conducting liquids, a first electrode in contact with the conducting liquid, a second electrode insulated from the conducting liquid, wherein the liquid interface is movable by electrowetting according to a change in a voltage applied between the first and second electrodes.

In some embodiments of the first aspect, the invention provides an intraocular variable focus implant wherein the non-conducting liquid comprises a mixture of compounds wherein at least one of the compounds has a melting temperature above intraocular temperature.

In some embodiments of the first aspect, the invention provides an intraocular variable focus implant wherein the non-conducing liquid has a melting temperature above 20° C.

In some embodiments of the first aspect, the invention provides an intraocular variable focus implant wherein the non-conducing liquid has a melting temperature above 10° C.

In some embodiments of the first aspect, the invention provides an intraocular variable focus implant comprising a first flexible transparent film comprising a hydrophilic surface in contact with the conducting liquid, and a second flexible transparent film comprising a hydrophobic surface in contact with the non-conducting liquid.

In some embodiments of the first aspect, the invention provides an intraocular variable focus implant comprising one or more structural films sealed to the first and second flexible transparent films, and one or more circuit components disposed the one or more structural films, wherein the first and second electrodes are disposed on the one or more structural films, and wherein the circuit components control the voltage applied.

In some embodiments of the first aspect, the invention provides an intraocular variable focus implant wherein the non-conducing liquid has a melting temperature above 20° C.

In some embodiments of the first aspect, the invention provides an intraocular variable focus implant wherein the non-conducting liquid comprises a mixture of compounds and wherein at least one of the compounds has a melting temperature above intraocular temperature.

In some embodiments of the first aspect, the invention provides an intraocular variable focus implant wherein one of the compounds in the non-conducting liquid acts as a membrane between the non-conducting and conducting liquids below the intraocular temperature and above 0° C.

In some embodiments of the first aspect, the invention provides an intraocular variable focus implant wherein the non-conducting liquid comprises one or more compounds selected from the list consisting of a linear alkane [$C_nH_{2n+2}$] where n is greater than 15 and less than 22, a diphenyl alkane [$C_nH_{2n}$—$(C_6H_5)_2$] where n is greater than 1 and less than 5, vinyl triphenylsilane, diphenylsulfide, palmitic acid, 1,4,-diter-butylbenzene, 1-methylfluoene, 9,10-dihydroanthracene, fluorene, methyltriphenylsilane, allyltriphenylsilane, ethyltriphenylsilane, and a cycloalkane $C_nH_{2n}$ where n is greater than 6 and less than 15.

In some embodiments of the first aspect, the invention provides an intraocular variable focus implant wherein the non-conducting liquid comprises less than 20% by weight of phenyltrimethyl germane, diphenyldimethylgermane, or a mixture thereof.

In some embodiments of the first aspect, the invention provides an intraocular variable focus implant wherein more than 80% by weight of the compounds have a melting temperature between 10° C. and 37° C.

In some embodiments of the first aspect, the invention provides an intraocular variable focus implant wherein the non-conducting liquid contains less than 20% by weight of organosilanes.

In some embodiments of the first aspect, the invention provides an intraocular variable focus implant wherein the intraocular variable focus implant is maintained at a temperature below the melting temperature of the compound while the compound, in liquid form, is disposed into the intraocular variable focus implant.

In a second aspect, the invention provides a method of manufacturing a variable focus implant, the method comprising: disposing in the implant a non-conducting liquid with a melting temperature above 0° C., and disposing in the implant a conducting liquid, wherein a liquid interface is formed by the non-conducting and conducting liquids and the liquid interface is movable by electrowetting according to a change in a voltage applied between a first and second electrode.

In some embodiments of the second aspect, the invention provides a method comprising: disposing the non-conducting liquid at a temperature above the melting temperature of the non-conducting liquid, and cooling the non-conducting liquid to below the melting temperature of the non-conducting liquid.

In some embodiments of the second aspect, the invention provides a method wherein the non-conducting liquid comprises a mixture of compounds wherein at least one of the compounds has a melting temperature above intraocular temperature.

In some embodiments of the second aspect, the invention provides a method comprising: disposing one compound of the mixture of compounds at a temperature above the melting temperature of the one compound, and cooling the one compound to below the melting temperature of the one compound.

In some embodiments of the second aspect, the invention provides a method comprising: disposing a first compound of the mixture of compounds at a temperature above the melting temperature of the first compound, cooling the first compound to below the melting temperature of the first compound, disposing a second compound of the mixture of compounds at a temperature below the melting temperature of the first compound and above the melting temperature of the second compound, and cooling the second compound to below the melting temperature of the second compound.

In some embodiments of the second aspect, the invention provides a method wherein the second compound is disposed in liquid form while the intraocular variable focus implant is maintained at a temperature below the melting temperature of the compound.

In some embodiments of the second aspect, the invention provides a method wherein the non-conducing liquid has a melting temperature above 20° C.

In some embodiments of the second aspect, the invention provides a method wherein the non-conducing liquid has a melting temperature above 10° C.

In some embodiments of the second aspect, the invention provides a method wherein one of the compounds in the non-conducting liquid acts as a membrane between the non-conducting and conducting liquids below the intraocular temperature and above 0° C.

In some embodiments of the second aspect, the invention provides a method wherein the non-conducting liquid comprises one or more compounds selected from the list consisting of a linear alkane $[C_nH_{2n+2}]$ where n is greater than 15 and less than 22, a diphenyl alkane $[C_nH_{2n}—(C_6H_5)_2]$ where n is greater than 1 and less than 5, vinyl triphenylsilane, diphenylsulfide, palmitic acid, 1,4,-di-ter-butylbenzene, 1-methylfluoene, 9,10-dihydroanthracene, fluorene, methyltriphenylsilane, allyltriphenylsilane, ethyltriphenylsilane, and a cycloalkane $C_nH_{2n}$, where n is greater than 6 and less than 15.

In some embodiments of the second aspect, the invention provides a method wherein the non-conducting liquid comprises less than 20% by weight of phenyltrimethyl germane, diphenyldimethylgermane, or a mixture thereof.

In some embodiments of the second aspect, the invention provides a method wherein more than 80% by weight of the compounds have a melting temperature between 10° C. and 37° C.

In some embodiments of the second aspect, the invention provides a method wherein the non-conducting liquid contains less than 20% by weight of organosilanes.

In a third aspect, the invention provides an intraocular variable focus implant comprising: a conducting liquid with a melting temperature below intraocular temperature and above 0° C., a non-conducting liquid, a liquid interface formed by the non-conducting and conducting liquids, a first electrode in contact with the conducting liquid, a second electrode insulated from the conducting liquid, wherein the liquid interface is movable by electrowetting according to a change in a voltage applied between the first and second electrodes.

In some embodiments of the third aspect, the invention provides an intraocular variable focus implant wherein the conducing liquid has a melting temperature above 20° C. and bellow 37° C.

In some embodiments of the third aspect, the invention provides an intraocular variable focus implant wherein the conducing liquid has a melting temperature above 10° C. and bellow 37° C.

In some embodiments of the third aspect, the invention provides an intraocular variable focus implant wherein the conducting liquid comprises less than 10% by weight of a gelling agent.

In some embodiments of the third aspect, the invention provides an intraocular variable focus implant wherein the gelling agent is selected from the list consisting of alginic acid, sodium alginate, potassium alginate, ammonium alginate, calcium alginate, gelatin, furcellaran or polysaccharides like agarose, carrageenan, pectin, or a mixture thereof.

In some embodiments of the third aspect, the invention provides an intraocular variable focus implant wherein the conducting liquid comprises a mixture of compounds wherein at least one of the compounds has a melting temperature above intraocular temperature.

In some embodiments of the third aspect, the invention provides an intraocular variable focus implant wherein one of the compounds in the conducting liquid acts as a membrane between the non-conducting and conducting liquids below the intraocular temperature and above 0° C. and melt into the conducting liquid at a temperature below intraocular temperature.

In a fourth aspect, the invention provides an intraocular variable focus implant comprising: a conducting liquid, a non-conducting liquid, a compound forming a solid interface between the non conducting and conducting liquids, and being soluble in the non conducting liquid at the intraocular temperature, a first electrode in contact with the conducting liquid, a second electrode insulated from the conducting liquid, wherein the liquid interface is movable by electrowetting according to a change in a voltage applied between the first and second electrodes.

In a fifth aspect, the invention provides an intraocular variable focus implant comprising: a conducting liquid, a non-conducting liquid, a compound forming a solid interface between the non conducting and conducting liquids, and being soluble in the conducting liquid at the intraocular temperature, a first electrode in contact with the conducting liquid, a second electrode insulated from the conducting liquid, wherein the liquid interface is movable by electrowetting according to a change in a voltage applied between the first and second electrodes.

In some embodiments of the first aspect, the invention provides an intraocular variable focus implant wherein a solid interface is formed between conducting and non conducting liquid, said solid interface being soluble in at least one liquid.

DETAILED DESCRIPTION

Figure 1:
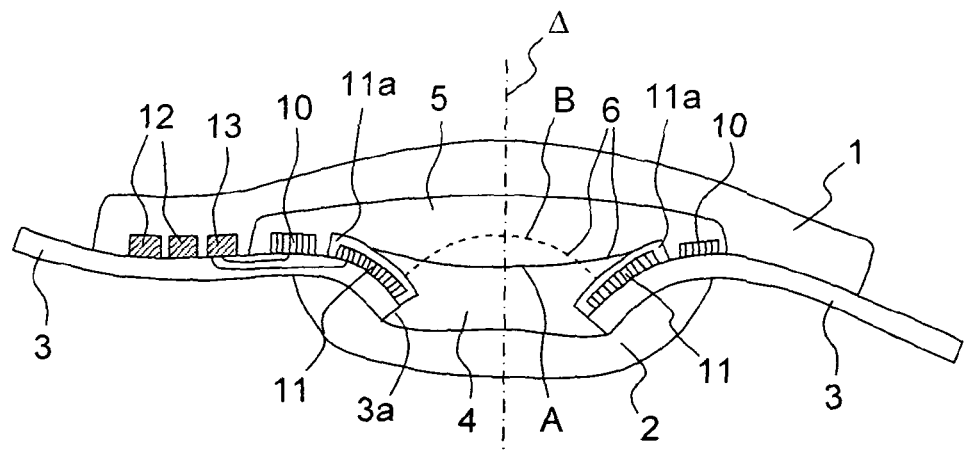
FIG. 1 shows an electrowetting based IOL in accordance with one or more embodiments of the claimed invention.

Specific embodiments of the invention will now be described in detail with reference to the accompanying figures. Like elements in the various figures are denoted by like reference numerals for consistency. Further, the use of "Fig." in the drawings is equivalent to the use of the term "Figure" in the description.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Embodiments of the claimed invention relate to an intraocular liquid (IOL) lens that contains two immiscible liquids in contact, without any physical separation between liquids. IOL devices are typically scrolled or folded prior to injection in the eye, to operate as non-invasively as possible. If such an IOL is a liquid lens, the scrolling or folding operation is likely to move liquids out of their confinement area or disperse on liquid in the other due to shear stress and, thus, degrade the performance of the liquid lens. One or more embodiments of the invention relate to a liquid lens and method of manufacturing a liquid lens that remains undisturbed by scrolling or folding.

European Patent EP1996968 from Varioptic is hereby incorporated by reference in its entirety. EP1996868 describes an IOL based on electrowetting actuation and made of two immiscible liquids standing on an insulating and hydrophobic surface, encapsulated in a foldable structure.

EP1996968 does not disclose the fluids used in such a IOL device or how to fold the device without disturbing the liquid's confinement. One of the issues associated with IOL devices is the ability of the device to be folded in order to reduce ocular incision. The present invention provides a solution to this technical issue.

In one or more embodiments of the invention, an IOL device based on electrowetting actuation, containing two immiscible liquids, enables device folding prior to injection into the patient eye without disturbing the liquid's confinement.

In one or more embodiments of the invention, there are two liquids, one conducting and the other non-conducting. The non-conducting liquid is in a solid state while lens is folded and injected in the patient's eye. Then, the fluid becomes a liquid state once in the patient eye, at intraocular temperature (typically between 33° C. and 37° C. using an ambient air temperature of 20° C.).

In one or more embodiments of the invention, the non-conducting liquid has a melting temperature below intraocular temperature and above 0° C. In one or more embodiments, the melting temperature of the non-conducting liquid is above 10° C. In one or more embodiments, the melting temperature of the non-conducting liquid is above 20° C.

Because the non-conducting liquid is solid during folding process, it is unlikely that it will move out of its confinement area, and embodiments of the IOL device in the present invention may be injected through a reduced corneal incision while having an optimized performance.

In one or more embodiments of the invention, a membrane made of a non-conducting compound, may separate the non-conducting and conducting fluid during the folding and injection process.

In one or more embodiments of the invention, the conducting liquid has a melting temperature below intraocular temperature and above 0° C. In one or more embodiments, the melting temperature of the conducting liquid is above 10° C. In one or more embodiments, the melting temperature of the conducting liquid is above 20° C.

In one or more embodiments of the invention, a membrane made of a polar compound, may separate the non-conducting and conducting fluid during the folding and injection process and melt in the conducting fluid below intraocular temperature.

In one or more embodiments of the invention, either the conducting or non-conducting liquid may include a gelling agent, forming a gel when incorporated, or dissolved, into the liquid, and having a melting temperature below intraocular temperature and above 0° C. In one or more embodiments, the melting temperature of the jellified fluid is above 10° C. In one or more embodiments, the melting temperature of the jellified fluid is above 20° C.

In one or more embodiments of the invention, the conducting liquid may contain a gelling agent like alginic acid, sodium alginate, potassium alginate, ammonium alginate, calcium alginate, gelatin, furcellaran or polysaccharides like agarose, carrageenan, or pectin.

FIG. 1 shows an ophthalmic implant as described in European patent application EP1996968, in accordance with one or more embodiments of the claimed invention. The implant is made from transparent and flexible materials, examples include, but are not limited to, transparent polymers like polymethyl methacrylate (PMMA), polycarbonate, epoxies, polyesters, fluoropolymers, fluorinated ethylene propylene (FEP), PTFE (polytetrafluoroethylene), polyolefins, and polycycloolefins. Inside the implant, two liquids are trapped: the first liquid (4) is a non-polar liquid, non-conducting (or insulating liquid) forming a drop inside the capsule. The second liquid (5) is a conducting polar liquid (may be based on water solution). Both liquids are immiscible, with approximately the same density, and different indices of refraction. A first electrode (11) in the shape of a ring may be covered with a thin insulator film (2) for electrowetting actuation. In the embodiment described in FIG. 1, the thin insulator film (2) is also playing the role of the capsule window. A second electrode (10) is in direct contact with the conducting liquid (5).

Electrowetting actuation is used to activate the lens. Using a control signal, a voltage is applied between electrodes (10) and (11). The voltage induces an electrowetting effect, thus changing the contact angle of the drop of liquid (4), passing from shape A (flat drop) to shape B (a more curved drop). Because the indices of refraction of the two liquids are different, the device forms a variable power lens. In one or more embodiment of the invention, the dioptre variation may range from a few dioptres to several tens of dioptres.

Figure 2:
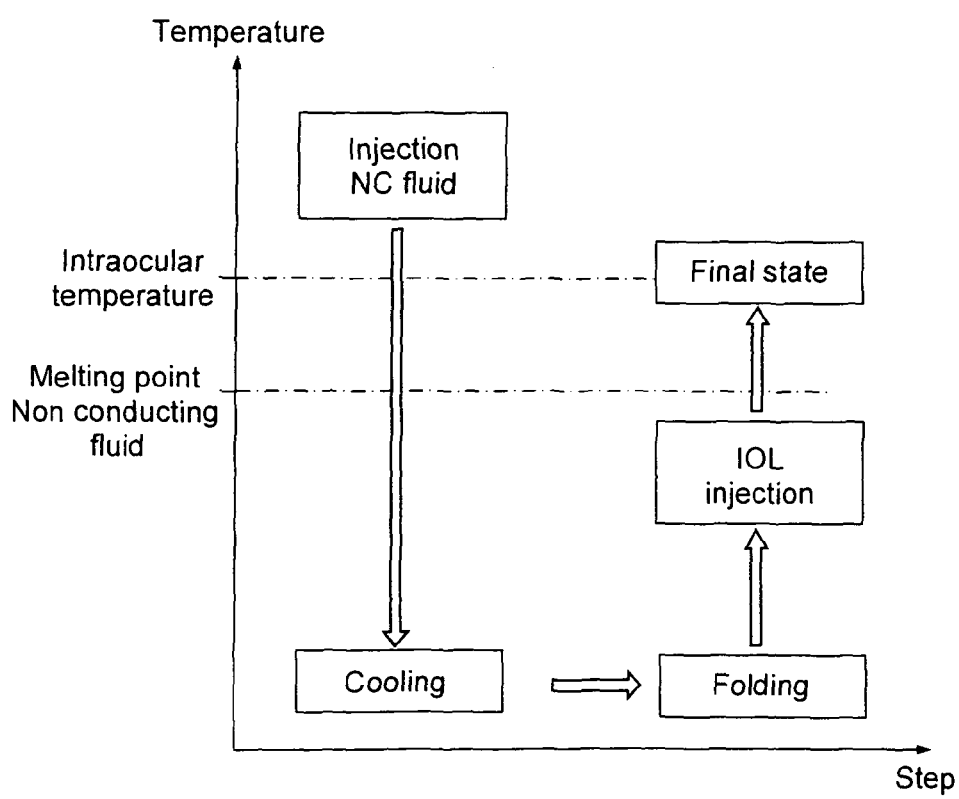
FIG. 2 shows a schematic view of a process to fill, fold and inject an IOL using a single non-conducting fluid in accordance with one or more embodiments of the invention.

In one or more embodiments of the invention, the non-conducting fluid includes one or more non-conducting compounds with a melting temperature below intraocular temperature, and above the temperature during the injection process. FIG. 2 is a schematic of the process in accordance with one or more embodiments of the invention. Table 1 describes several compounds with corresponding melting temperatures. Examples of specific conducting and non-conducting fluids in accordance with one or more embodiments of the invention are given in formulations 1 and 4 (respectively conducting and non-conducing fluids), formulations 2 and 5, and formulations 3 and 6. However, the claimed invention is not limited to these specific combinations of conducting and non-conduction fluids. The liquid lens may filled with both conducting and non-conducting fluids at a temperature above melting temperature, then cooled until the non-conducting fluid is solidified. IOL may then be scrolled or folded at a temperature below the melting point temperature in preparation for surgery. Once the IOL is within the patient's eye, and unfolded, the non-conducting fluid melts and the liquid lens becomes operational.

TABLE 1

List of compounds and corresponding melting temperature

| Name | mp (° C.) |
|---|---|
| Hexadecane | 18.1 |
| diphenyl methane | 26 |
| Octadécane | 27.8 |
| Nonadécane | 32.1 |
| Diphenylethane | 50 |
| Vinyltriphenylsilane | 58 |
| Diphenyl disulfide | 58 |
| Palmitic acid | 62 |
| 1,4-Di-tert-butylbenzene | 77 |
| 1-Methylfluorene | 84 |
| 9,10-Dihydroanthracene | 105 |
| Fluorene | 116 |
| Methyltriphenylsilane | <30 |
| Allyltriphenylsilane | 88 |
| Cyclooctane | 10 |
| Cyclohexane | 6.5 |
| hexadecahydropyrene | <30 |
| Eicosane | 41 |
| Cyclododecane | <30 |

Conducing Fluid Formulation 1

| compound | Weight % |
|---|---|
| Sodium Bromide | 0.86% |
| water | 97.64% |
| polypropylene glycol | 0.50% |
| 1-Pentanol | 1.00% |

| measurement | value |
|---|---|
| density (g/cm3) | 0.9968 |
| refractive index at 589 nm at 20° C. | 1.33571 |
| Viscosity at 20° C. (mm²/s) | 1.5065 |

Conducing Fluid Formulation 2

| compound | Weight % |
|---|---|
| Sodium Bromide | 1.43% |
| water | 97.07% |
| polypropylene glycol | 0.50% |
| 1-Pentanol | 1.00% |

| measurement | value |
|---|---|
| density (g/cm3) | 1.005 |
| refractive index at 589 nm at 20° C. | 1.337 |
| Viscosity at 20° C. (mm²/s) | 1.040 |

Conducing Fluid Formulation 3

| Compound | weight % |
|---|---|
| Sodium Bromide | 2.01% |
| Water | 96.49% |
| polypropylene glycol | 1.00% |
| 1-Pentanol | 0.50% |

| Measurement | value |
|---|---|
| density (g/cm3) | 1.0078 |
| refractive index at 589 nm at 20° C. | 1.3377 |
| Viscosity at 20° C. (mm²/s) | 1.0395 |

Non-Conducing Fluid Formulation 4

| Compound | weight % |
|---|---|
| Diphenylmethane | 90.00% |
| Diphényldiméthylgermane | 5.00% |
| Hexadecane | 5.00% |

| measurement | value |
|---|---|
| density (g/cm3) | 0.9963 |
| refractive index at 589 nm at 20° C. | 1.5701 |
| Viscosity at 20° C. (mm²/s) | 2.6973 |
| Melting point (° C.) | >15° C. |

Non-Conducing Fluid Formulation 5

| compound | weight % |
|---|---|
| diphenylmethane | 91.80% |
| diphényldiméthylgermane | 6.20% |
| Hexadecane | 2.00% |

-continued

| measurement | value |
| --- | --- |
| density (g/cm3) | 1.0052 |
| refractive index at 589 nm at 20° C. | 1.5743 |
| Viscosity at 20° C. (mm²/s) | 2.6778 |
| Melting point (° C.) | >15° C. |

Non-Conducing Fluid Formulation 6

| compound | weight % |
| --- | --- |
| diphenylmethane | 71.5% |
| diphényldiméthylgermane | 18.5% |
| Hexadecane | 10.0% |

| measurement | value |
| --- | --- |
| density (g/cm3) | 1.0083 |
| refractive index at 589 nm at 20° C. | 1.5621 |
| Viscosity at 20° C. (mm²/s) | 2.9330 |
| Melting point (° C.) | 15 |

In one or more embodiments of the invention, the conducting fluid comprises water and at least one organic or inorganic ion, typically at least one organic or inorganic ionic or ionizable salt, or a mixture thereof, conferring conductive properties to said fluid.

In the following specification, "ionic salts" refers to salts that are totally or substantially totally dissociated (such as a bromine-anion and a cation) in water. "ionizable salts" refers to salts that are totally or substantially totally dissociated in water, after chemical, physical or physico-chemical treatment.

Ions that are suitable in the present invention include both cations and anions, which may be simultaneously, but not necessarily, present together in the conducting fluid. Examples of anions include, but are not limited to, halides, e.g. chloride, bromide, iodide, sulphate, carbonate, hydrogen carbonate, acetate, and the like, as well as mixtures thereof. Examples of cations include, but are not limited to alkali, and alkaline-earth.

Organic and inorganic ionic and ionizable salts are thus well known in the art, and examples of these include, but are not limited to potassium acetate, magnesium chloride, zinc bromide, lithium bromide, sodium bromide, lithium chloride, calcium chloride, sodium sulphate, sodium dibasic phosphate, sodium monobasic phosphate, phosphoric acid, acetic acid, sodium acetate, carboxylic acid (RCOOH, where R being an alkyl group $C_{2n}H_{2n+1}$, with n being between 1 and 10) and corresponding sodium carboxylate salt, phosphocholine salt and the like, as well as mixtures thereof.

Mixtures of one or more ionic salts together with one or more ionizable salts are also encompassed by the present invention.

As already mentioned, the conductive fluid comprises an organic or inorganic ionic or ionizable salt. Said salt is dissolved in water. Water to be used in the conductive fluid should be as pure as possible, i.e. free, or substantially free, of any other dissolved components that could alter the optical properties of the optical electrowetting device, namely an optical lens driven by electrowetting. Ultra pure water is most preferably used. The concentration of the dissolved salt in the conductive fluid may vary in large proportions, keeping in mind a too high concentration may result in undesirable increase of density, refractive index, turbidity, haze, or loss of transparency for the optical device, lens or else.

Figure 3:
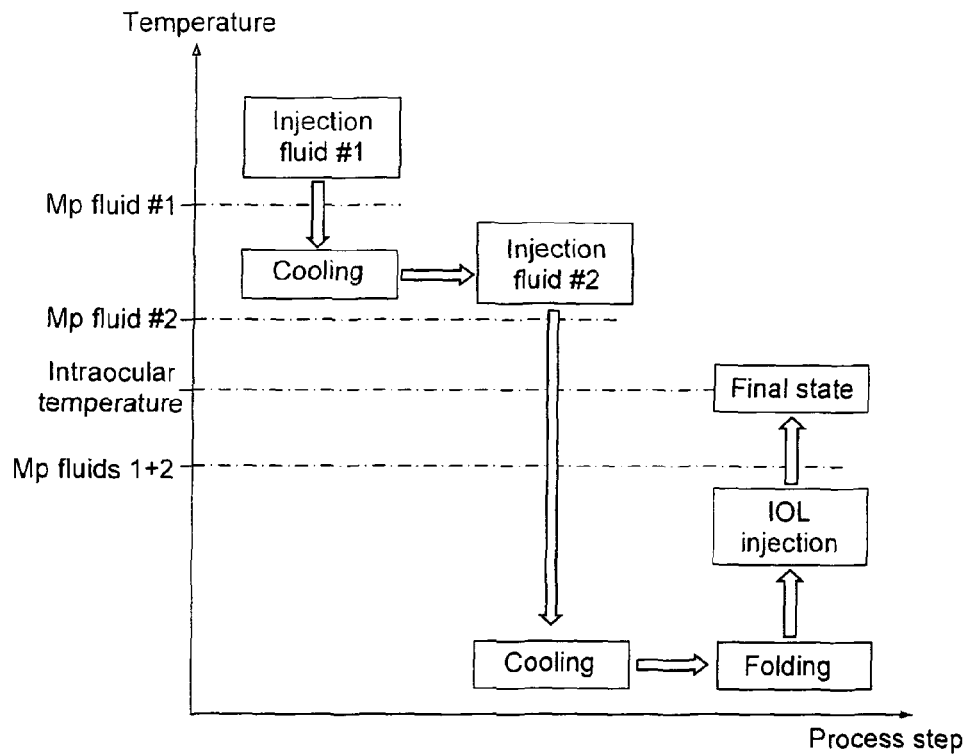
FIG. 3 shows a schematic view of a process to fill, fold and inject an IOL using two separate non-conducting fluids, both having a melting temperature above intraocular temperature in accordance with one or more embodiments of the invention.

In one or more embodiments of the invention, the non-conducting fluid is a mixture of compounds, where at least one compound has a melting temperature above intraocular temperature, but the mixture thereof has a melting temperature below intraocular temperature. This is possible because most liquids have a melting temperature depression when mixed with other compounds, when all compounds are miscible. FIG. 3 shows a schematic of the process in accordance with one or more embodiments of the invention. Compounds having the highest melting temperature may be injected in the liquid lens at a temperature above its melting temperature then cooled to a temperature above melting point of the next compound to be injected. At this stage, the injected compounds may have been solidified as a result of the cooling. Therefore, all compounds may be injected separately. The order of injection may be from the highest melting point to the lowest melting point. When the last compound is injected, the IOL may be cooled until the non-conducting fluid is fully solidified. IOL may be folded at temperature below melting point temperature and is ready for the surgery operation. Once the IOL is within the patient eye, and unfolded, the non-conducting fluid compounds melt, mix together, and liquid lens becomes operational. One specific example of the above embodiment is the formulation 1 and 7; however, the above embodiment is not limited as such.

Non-Conducing Fluid Formulation 7

| compound | weight % |
| --- | --- |
| diphenylmethane | 81.00% |
| Vinyltriphenylsilane | 14.00% |
| Cyclodecane | 5.00% |

| measurement | value |
| --- | --- |
| density (g/cm3) | 0.9978 |

Figure 4:
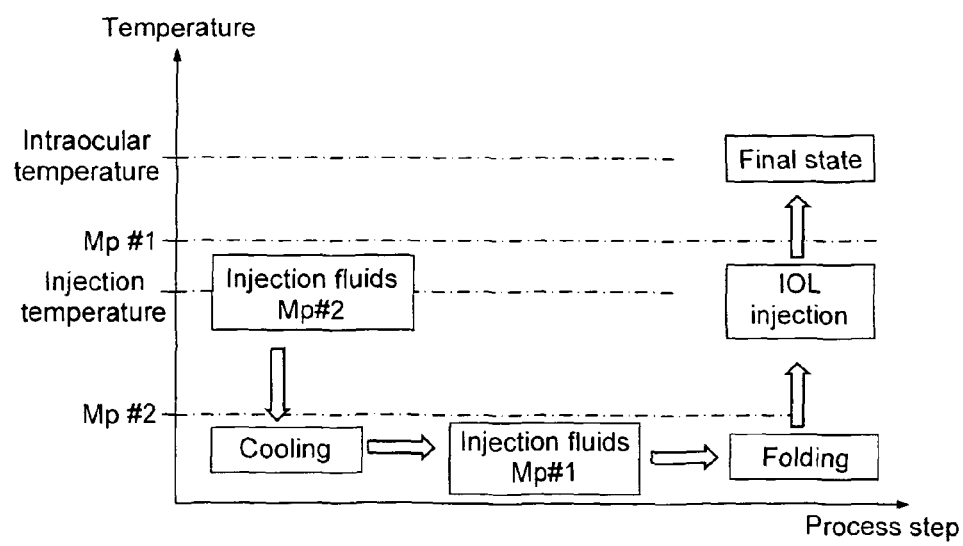
FIG. 4 shows a schematic view of a process to fill, fold and inject an IOL according to the present invention, using two separate non-conducting fluids, one having a melting temperature below injection temperature, the other one having a melting temperature above injection temperature in accordance with one or more embodiments of the invention.

FIG. 4 is a schematic of a process to fill, fold and inject an IOL using two separate non-conducting fluids, where one has a melting temperature (MP#2) below injection temperature and the other has a melting temperature (MP#1) above injection temperature, but below the intraocular temperature in accordance with one or more embodiments of the invention. The fluid having the lowest melting temperature, below injection temperature, is injected in the liquid lens at a temperature above its melting temperature, and then cool down until solidification. That fluid is kept at a temperature below melting temperature of the other compounds. Then a fluid having a melting temperature between the injection temperature and the intraocular temperature is injected and, thus, solidified at the surface of the first injected compounds. Therefore, in accordance with one or more embodiments of the invention, the fluids may be injected separately with the fluid having the highest melting temperature physically located at the interface between the conducting fluid and the other non-conducting fluid. Examples of the conducting and non-conducting fluids that may be used include, but are not limited to, the formulations 1 and 8 and formulations 3 and 9.

Non-Conducing Fluid Formulation 8

| compound | weight % |
|---|---|
| Phenyltrimethylgermane | 55%. |
| SIP 6827,0 | 25%. |
| Hexadecane | 20%. |

| measurement | value |
|---|---|
| density (g/cm3) | 0.9980 |
| refractive index at 589 nm at 20° C. | 1.4744 |
| Viscosity at 20° C. (mm$^2$/s) | 1.8834 |

Non-Conducing Fluid Formulation 9

| compound | weight % |
|---|---|
| diphényldiméthylgermane | 52.50% |
| SIP 6827,0 | 17.50% |
| Hexadecane | 30.00% |

| measurement | value |
|---|---|
| density (g/cm3) | 1.0080 |
| refractive index at 589 nm at 20° C. | 1.5067 |
| Viscosity at 20° C. (mm$^2$/s) | 4.0537 |

In one or more embodiment of the present invention, the non conducting fluid is injected in the liquid lens at a temperature above its melting temperature, and then cool down until solidification. A further compound is then deposited on the solidified non-conducting fluid prior to the conducting fluid injection to form a solid membrane. The membrane remains solid during the folding process and injection but is soluble in the conducting or the non-conducting fluid at intraocular temperature after injection in the patient's eye.

In one or more embodiment of the present invention, the solid membrane is made of water soluble polymers like hydroxyethylcellulose, ethylcellulose polymers, cellulose ethers, Poly(Acrylic Acids), Polyvinyl alcohol, or water soluble resins, or hydrocarbon soluble polymers.

In one or more embodiment of the present invention, the solid membrane formed between the conducting and non conducting fluids is made soluble in fluids by irradiation during the capsulotomy operation.

The IOL may then be folded at temperature below melting point temperature of the compounds at the interface and warmed up at the injection temperature. The fluid at the interface may act as a membrane between the conducting fluid and the other non-conducting fluid that has a melting temperature below the injection temperature. At this point, the IOL is ready for surgical implantation. Once the IOL is within the patient's eye and unfolded, the non-conducting fluids may melt and mix together. At this point, the liquid lens becomes operational.

In one or more embodiments of the invention, the insulating coating may be made of poly-para-xylylene linear polymers, for example, Parylene C; Parylene N, Parylene VT4, and Parylene HT.

In one or more embodiments of the invention, the insulating coating may be coated with a thin layer of a low surface energy coating such as Teflon® or Fluoropel®.

Table 1 is a list of compounds that may be used in the present invention.

In one or more embodiments of the invention, the non conductive fluid may contain a linear alkane ($C_nH_{2n+2}$, where 22>n>15, such as hexadecane, nonadecane, eicosane), a diphenyl alkane ($C_2H_{2n}$—$(C_6H_5)_2$, where 5>n>1, such as diphenylmethane, diphenylethane), or vinyl triphenylsilane.

In one or more embodiments of the invention, the non-conductive fluid may contain one or more of the following specific compounds: diphenylsulfide, palmitic acid, 1,4-Diter-butylbenzene, 1-methylfluorene, 9,10-Dihydroanthracene, and Fluorene.

In one or more embodiments, the non-conductive fluid may contain one or more cycloalkane $C_nH_{2n}$, where 6<n<15, such as cyclooctane, cyclohexane, or cyclododecane.

In one or more embodiments, the non-conductive fluid may contain one or more organosilanes of formula Si—$(R)_4$, where at least three of the R groups are represented independently by (hetero)aryl, (hetero)arylalkyl, (hetero)arylalkenyl and (hetero)arylalkynyl. In such embodiments, the at least one of the R groups may be an alkyl ($C_nH_{2n+1}$) or alkene group ($C_nH_{2n-1}$), where n=1, 2 or 3. Examples include, but are not limited to methyltriphenylsilane, allyltriphenylsilane, and ethyltriphenylsilane.

The non-conductive fluid may contain one or more germane based species, for example hexamethyldigermane, diphenyldimethylgermane, and phenyltrimethyl-germane.

Table 2 describes mixtures of compounds depending on temperature and indicates when mixture is in solid and liquid state in accordance with one or more embodiments of the invention. The solid state should be used during folding and injection. In particular Table 2 demonstrates that a small amount of compound having a very low melting temperature (for example <20° C. for phenyltrimethyl germane) mixed with a large amount of a high melting temperature compound (for example diphenylmethane) will result in a mixture with a melting temperature in the required range, i.e. between 10° C. and 32° C.

TABLE 2

State diagram for various mixtures of non conducting fluids (solid: S; Liquid: L)

| Composition | −20° C. | −2° C. | +10° C. | +15° C. | +18° C. | +25° C. |
|---|---|---|---|---|---|---|
| Diphenylmethane | S | S | S | S | S | S |
| 10% phenylgermane + 90% diphenylmethane | S | S | S | S + L | S + L | L |
| 30% phenylgermane + 70% diphenylmethane | S | S + L | S + L | L | L | L |
| 70% phenylgermane + 30% diphenylmethane | S + L | S + L | S + L | L | L | L |
| Phenylgermane | L | L | L | L | L | L |
| 5% diphenylgermane + 95% diphenylmethane | S | S | S | S + L | S + L | L |
| 10% diphenylgermane + 90% diphenylmethane | S | S | S + L | S + L | S + L | L |
| 20% diphenylgermane + 80% diphenylmethane | S | S | S + L | S + L | S + L | L |

TABLE 2-continued

State diagram for various mixtures of non conducting fluids (solid: S; Liquid: L)

| Composition | −20° C. | −2° C. | +10° C. | +15° C. | +18° C. | +25° C. |
|---|---|---|---|---|---|---|
| formulation 4 | S | S | S | S + L | S + L | L |
| formulation 6 | S | S | S | S + L | L | L |

Embodiments of the invention may be used in any application that using a device containing two immiscible liquids, such that the liquids are contact with each other, and the device is folded during the application at a given temperature, and then unfolded at another temperature above the first temperature, where the liquids must be confined in a given volume, when the performance of the device may be disturbed and/or lowered if liquids are temporarily mixed during the folding and unfolding process.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An accommodative intraocular lens having a variable optical power and containing two immiscible liquids encapsulated in a foldable structure, said intraocular lens comprising:
    a non-conducting liquid having a melting temperature above 0° C. and having a liquid state at intraocular temperature;
    a conducting liquid;
    a liquid interface formed by the non-conducting and conducting liquids;
    a first electrode in contact with the conducting liquid; and
    a second electrode insulated from the conducting liquid,
    wherein the liquid interface is movable by electrowetting according to a change in a voltage applied between the first and second electrodes,
    wherein the foldable structure is filled with the conducting liquid and the non-conducting liquid at a temperature above the melting temperature of the non-conducting liquid,
    wherein the intraocular lens is configured to be cooled until the non-conducting liquid is solidified,
    wherein the intraocular lens is configured to be folded at a temperature below the melting temperature of the non-conducting liquid,
    wherein the intraocular lens is configured to be injected in a folded configuration through a reduced corneal incision,
    wherein the intraocular lens is configured to be within a patient's eye, in which the solidified non-conducting liquid melts and the intraocular lens unfolds and becomes operational.

2. The accommodative intraocular lens of claim 1, wherein the non-conducting liquid comprises a mixture of compounds wherein at least one of the compounds has a melting temperature above an intraocular temperature.

3. The accommodative intraocular lens of claim 2, wherein one of the compounds in the non-conducting liquid acts as a membrane between the non-conducting and conducting liquids below the intraocular temperature and above 0° C.

4. The accommodative intraocular lens of claim 2, wherein more than 80% by weight of the compounds have a melting temperature between 10° C. and 37° C.

5. The accommodative intraocular lens of claim 2, wherein the non-conducting liquid contains less than 20% by weight of organosilanes.

6. The accommodative intraocular lens of claim 1, wherein the non-conducting liquid comprises one or more compounds selected from the group consisting of a linear alkane $[C_nH_{2n+2}]$ where n is greater than 15 and less than 22, a diphenyl alkane $[C_nH_{2n}-(C_6H_5)_2]$ where n is greater than 1 and less than 5, vinyl triphenylsilane, diphenylsulfide, palmitic acid, 1,4,-di-ter-butylbenzene, 1-methylfluoene, 9,10-dihydroanthracene, fluorene, methyltriphenylsilane, allyltriphenylsilane, ethyltriphenylsilane, and a cycloalkane $C_nH_{2n}$ where n is greater than 6 and less than 15.

7. The accommodative intraocular lens of claim 1, wherein the non-conducting liquid comprises less than 20% by weight of phenyltrimethyl germane, diphenyldimethylgermane, or a mixture thereof.

8. The accommodative intraocular lens of claim 1, wherein the non-conducting liquid comprises one or more compounds selected from the group consisting of a linear alkane $[C_nH_{2n+2}]$ where n is greater than 15 and less than 22, diphenylmethane, and a cycloalkane $C_nH_{2n}$ where n is greater than 6 and less than 15.

* * * * *